(12) United States Patent
Rioux et al.

(10) Patent No.: US 8,007,496 B2
(45) Date of Patent: Aug. 30, 2011

(54) METHOD OF THERAPEUTICALLY TREATING TISSUE WHILE PREVENTING PERFUSION/VENTILATION OF THE TISSUE

(75) Inventors: Robert F. Rioux, Ashland, MA (US); Jeffrey V. Bean, Fitchburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1251 days.

(21) Appl. No.: 11/420,697

(22) Filed: May 26, 2006

(65) Prior Publication Data

US 2007/0276362 A1    Nov. 29, 2007

(51) Int. Cl.
*A61B 18/04* (2006.01)
*A61B 18/18* (2006.01)
*A61F 7/12* (2006.01)

(52) U.S. Cl. ............... 606/41; 607/101; 607/105

(58) Field of Classification Search ........... 607/101, 607/102, 105; 606/41, 20–23, 37; 604/103.06
See application file for complete search history.

(56) References Cited

U.S. PATENT DOCUMENTS

| | | | |
|---|---|---|---|
| 5,254,088 A | | 10/1993 | Lundquist et al. |
| 5,807,395 A * | | 9/1998 | Mulier et al. ............ 606/41 |
| 6,178,968 B1 * | | 1/2001 | Louw et al. ............ 128/898 |
| 6,190,353 B1 * | | 2/2001 | Makower et al. ......... 604/95.01 |
| 6,258,083 B1 * | | 7/2001 | Daniel et al. ............ 606/15 |
| 6,539,265 B2 * | | 3/2003 | Medhkour et al. ........... 607/99 |
| 7,189,231 B2 * | | 3/2007 | Clague et al. ............ 606/45 |
| 2002/0016564 A1 * | | 2/2002 | Courtney et al. ......... 604/96.01 |
| 2003/0018327 A1 * | | 1/2003 | Truckai et al. ............ 606/32 |
| 2003/0187389 A1 * | | 10/2003 | Morency et al. ......... 604/95.04 |
| 2007/0043350 A1 * | | 2/2007 | Soltesz et al. ............ 606/41 |

OTHER PUBLICATIONS

Oshima, Fumiyoshi et al., Lung Radiofrequency Ablation with and without Bronchial Occlusion: Experimental Study in Porcine Lungs, Journal of Vascular and Interventional Radiology 2003, vol. 15, No. 12, pp. 1451-1456, Dec. 2004.

* cited by examiner

*Primary Examiner* — Roy D Gibson
*Assistant Examiner* — Kaitlyn E Helling
(74) *Attorney, Agent, or Firm* — Vista IP Law Group LLP

(57) ABSTRACT

A method of treating a tissue region (e.g., a tumor) is provided. The method comprises introducing a delivery sheath within an anatomical conduit that supplies the tissue region with a fluid (e.g., blood or air). The anatomical conduit may be any naturally occurring conduit within a patient. The method further comprises expanding an occlusive device (e.g., a balloon) associated with the delivery sheath, such that the conduit is at least partially occluded to reduce the flow of fluid through the conduit. The method further comprises introducing a tissue treatment catheter within the delivery sheath, advancing the treatment catheter from the delivery sheath through an aperture in a wall of the conduit adjacent the tissue region, and conveying thermal energy from (i.e., hyperthermia) or to the treatment catheter (i.e., hypothermia) to treat (e.g., by ablating) the tissue region.

16 Claims, 8 Drawing Sheets

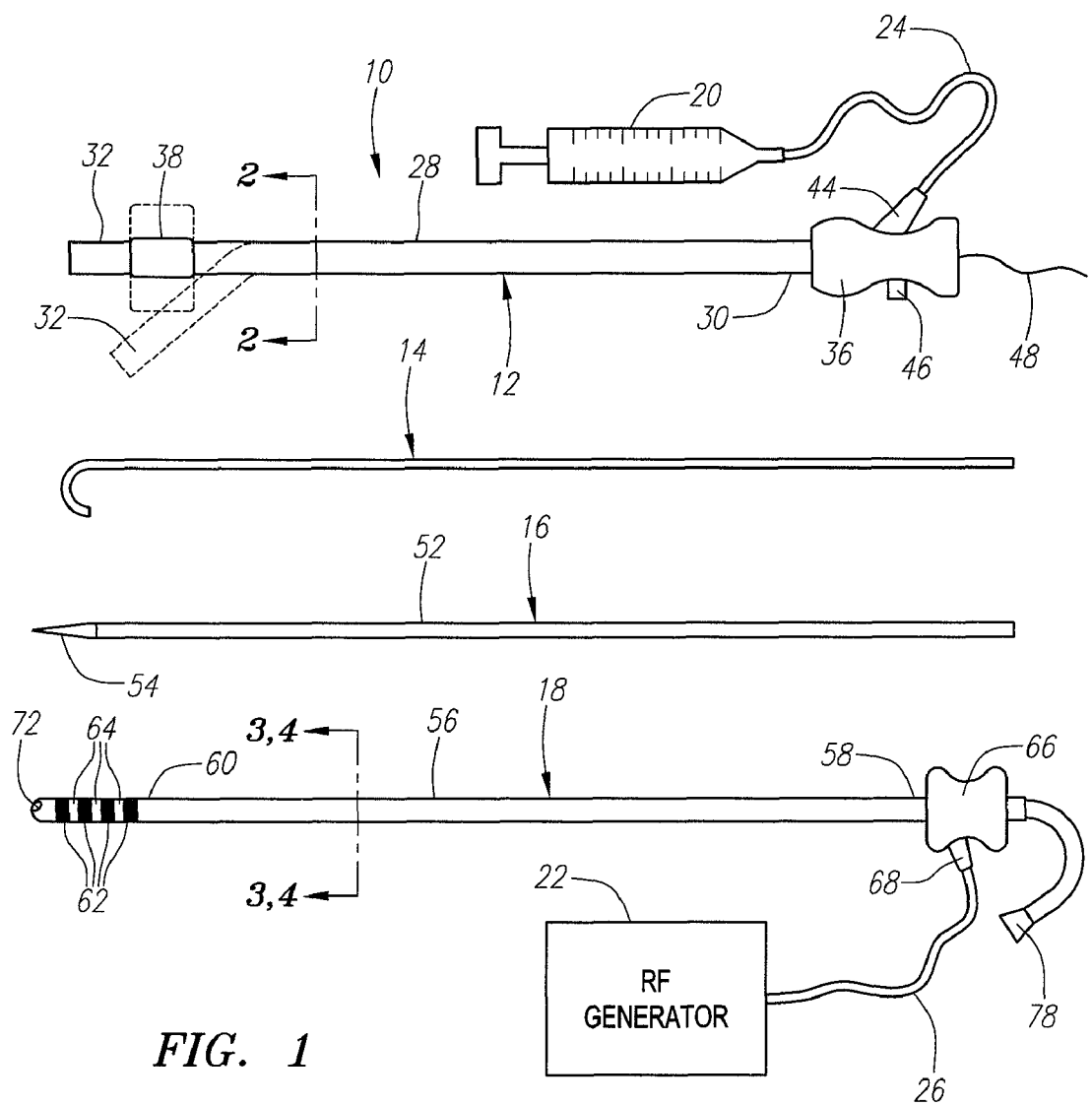
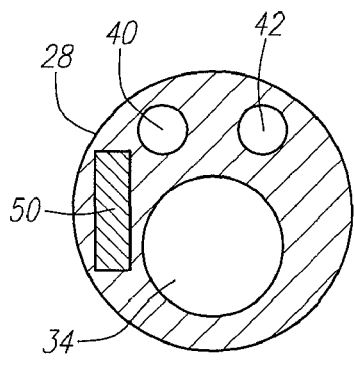
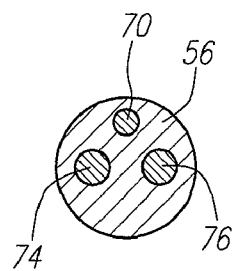
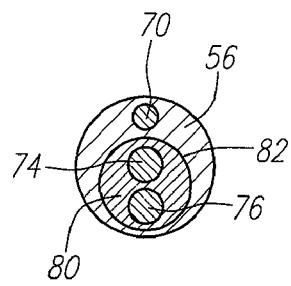
FIG. 1
FIG. 2   FIG. 3   FIG. 4

METHOD OF THERAPEUTICALLY TREATING TISSUE WHILE PREVENTING PERFUSION/VENTILATION OF THE TISSUE

FIELD OF THE INVENTION

The field of the invention relates to methods and apparatus for therapeutically ablating tissue using thermal energy, such as radio frequency (RF) energy.

BACKGROUND

Solid tissue tumors, such as neoplasms of the liver, kidney, bone, adrenal gland, and brain, traditionally have been treated with systematic chemotherapy, surgical resection, or local radiation therapy. Many tumors, however, remain poorly responsive to these therapeutic modalities, thereby necessitating the use of alternative treatments, such as thermal ablation of the tumor. Thermal sources for these treatment modalities include high-intensity ultrasound, laser, microwave, and radiofrequency (RF) energy. Of these different types of ablation techniques, RF ablation has proven to be safe, predictable, and inexpensive, and has emerged as the thermal ablation modality that most easily creates large volumes of tissue necrosis.

Although RF ablation of the tumor can be implemented during open surgery, it is most often performed percutaneously. One RF ablation technique utilizes a single needle electrode or a multiple needle electrode array that is inserted percutaneously using a surgical probe and guided with real-time ultrasound, computed tomography (CT) imaging, or magnetic resonance imaging (MRI) into the tumor. Once properly positioned, the needle electrode is activated, and alternating current is transferred from the needle electrode into the surrounding tissue, causing ionic agitation of the surrounding cells, ultimately leading to the production of frictional heat. As tissue temperatures increase between 60-100° C., there is an instantaneous induction of irreversible cellular damage referred to as coagulation necrosis. The treatment area may be monitored ultrasonographically for increased echogenicity during the procedure, which corresponds to the formation of tissue and water vapor microbubbles from the heated tissue and is used to roughly estimate the boundaries of the treatment sphere.

Recently, a number of experimental and clinical studies have demonstrated the feasibility and safety of lung tumor ablation. However, some studies have shown limitations in achieving complete necrosis in large tumors measuring 3 cm or more in diameter. See Oshima et al., *Lung Radiofrequency Ablation with and without Bronchial Occlusion: Experimental Study in Porcine Lungs*," Journal of Vascular and Interventional Radiology 2003, Vol. 15, No. 12. This is due, in large part, to the perfusion of blood through the lung tumor, which causes the conduction of thermal energy away from the target tissue and into the relatively cooler blood, thereby limiting the volume of the thermal lesion. In addition, a lung is composed of air spaces, and the air in the lungs is constantly flowing as a result of this ventilation. Thus, similar to effects of blood perfusion, the ventilation of air through lung tissue draws thermal energy away from the target tissue.

It is known to use a balloon to occlude a bronchial tube leading to the lung in which the target tissue is contained, which not only reduces the flow of air, but also reduces the perfusion of air, through the target tissue. A standard RF ablation probe can then be used to ablate the target tissue, which due to the reduced blood perfusion and air ventilation, creates a larger ablation lesion. While this procedure has been proven to be successful for ablating targeted lung tissue, it requires two separate devices (i.e., the occlusion catheter and the RF probe) with two different entry points (the patient's mouth and a percutaneous entry point through the patient's chest). As such, the complexity and invasiveness of such a procedure is increased.

For these reasons, it would be desirable to provide improved systems and methods for occluding the flow of fluid through a natural conduit within a patient's body, while delivering a therapeutic device via the natural conduit to a tissue treatment site to which the fluid would otherwise be supplied.

SUMMARY OF THE INVENTION

In accordance with the present inventions, a method of treating a tissue region (e.g., a tumor) is provided. The method comprises introducing a delivery sheath within an anatomical conduit that supplies the tissue region with a fluid (e.g., blood or air). The anatomical conduit may be any naturally occurring conduit within a patient. For example, if the tissue region is within a lung, the anatomical conduit may be a bronchial tube or a pulmonary artery. The method further comprises expanding an occlusive device (e.g., a balloon) associated with the delivery sheath, such that the conduit is at least partially occluded to reduce the flow of fluid through the conduit. In one method, the conduit is fully occluded to prevent the flow of fluid through the conduit.

The method further comprises introducing a tissue treatment catheter within the delivery sheath, advancing the treatment catheter from the delivery sheath through an aperture in a wall of the conduit adjacent the tissue region, and conveying thermal energy from (i.e., hyperthermia) or to the treatment catheter (i.e., hypothermia) to treat (e.g., by ablating) the tissue region. If the thermal energy is conveyed from the treatment catheter, such thermal energy may take the form of radio frequency (RF) energy.

An optional method further comprises introducing a stylet within the delivery sheath, and piercing the conduit wall to create the aperture. In this case, the treatment catheter may be conveniently advanced over the stylet through the aperture. Another optional method further comprises introducing a scope within the delivery sheath, and visualizing the tissue region with the scope. The scope may, e.g., be integrated with the treatment catheter or may be removably introduced within the treatment catheter. Still another optional method further comprises steering a distal end of the delivery sheath toward a region of the conduit wall through which the treatment catheter is to be advanced.

Other and further aspects and features of the invention will be evident from reading the following detailed description of the preferred embodiments, which are intended to illustrate, not limit, the present inventions.

BRIEF DESCRIPTION OF DRAWINGS

The drawings illustrate the design and utility of embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIG. 1 is a plan view of a tissue treatment system constructed in accordance with a preferred embodiment of the present invention;

FIG. 2 is a cross-sectional view of a delivery sheath used in the tissue treatment system of FIG. 1, taken along line 2-2;

FIG. 3 is a cross-sectional view of an ablation catheter used in the tissue treatment system of FIG. 1, taken along line 3-3;

FIG. 4 is a cross-sectional view of an alternative ablation catheter used in the tissue treatment system of FIG. 1, taken along line 4-4.

DETAILED DESCRIPTION OF THE ILLUSTRATED EMBODIMENTS

Figure 5A:
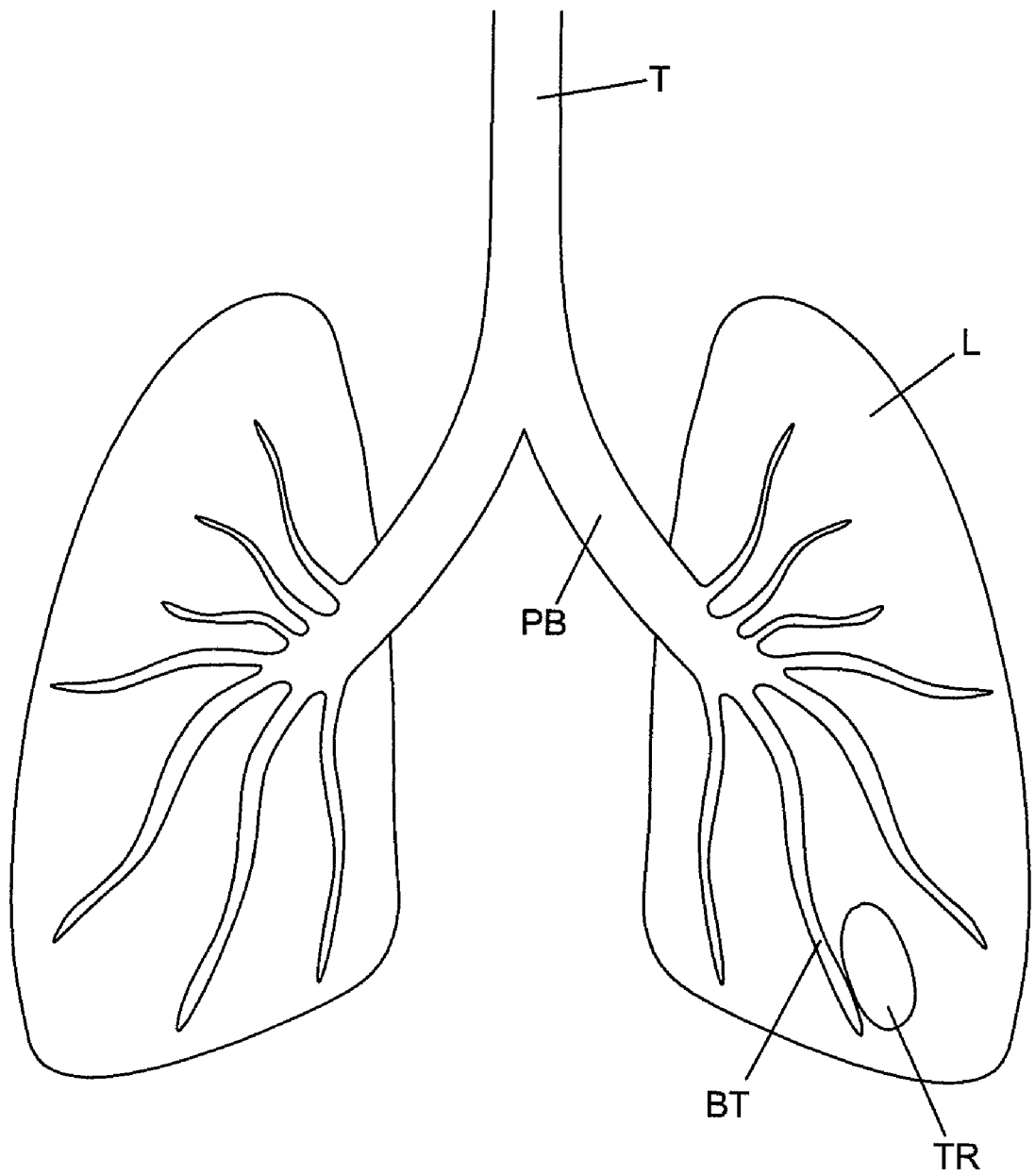
FIGS. 5A-5L are side views illustrating a method of treating a tumor contained within lung tissue of a patient using the system of FIG. 1.

Referring to FIG. 1, a tissue treatment system 10 constructed in accordance with one embodiment of the present invention will now be described. The tissue treatment system 10 generally comprises (1) a delivery sheath 12 that can be advanced through an anatomical conduit (such as a blood vessel, or air tube, such as a bronchial tube) that supplies fluid, such as blood or air to a tissue region, and occlude the anatomical conduit to reduce or prevent the flow of fluid through the conduit; (2) a guidewire 14 over which the delivery sheath 12 may be introduced; (3) a stylet 16 that can be introduced through the delivery sheath 12 to puncture a wall of the conduit; (4) a tissue treatment catheter, and in particular a radio frequency (RF) ablation catheter 18, that can be delivered through the delivery sheath 12 and advanced through the puncture within the conduit wall to ablate the tissue region; (5) a source of an inflation medium 20 configured for conveying an inflation medium under positive pressure to an conduit occlusion component of the delivery sheath 12 via a conduit 24; and (6) a tissue ablation source, and in particular a radio frequency (RF) generator 22, configured for supplying RF energy in a controlled manner to a tissue ablative component of the RF ablation catheter 18 via a RF cable 26.

The delivery sheath 12 comprises an elongated sheath body 28 having a proximal end 30, a distal end 32, and a delivery lumen 34 (shown in FIG. 2) extending through the sheath body 28 between the proximal end 30 and the distal end 32. As will be described in further detail below, the delivery lumen 34 is used to deliver the ablation catheter 18 and stylet 16 within the patient's body. The sheath body 28 has a suitable length, typically in the range from 40 cm to 200 cm, usually from 75 cm to 120 cm. The sheath body 28 has an outside diameter consistent with its intended use, typically being from 1 mm to 5 mm, usually from 2 mm to 4 mm. The sheath body 28 may be introduced over the movable guidewire 14. In the illustrated embodiment, the guidewire 14 will run through the delivery lumen 34 to provide an "over-the-wire" design. Alternatively, the sheath body 28 may have a "rapid exchange" or "monorail" design, in which case, the guidewire 14 can be received through a lumen (not shown) that extends only over a distal length of the sheath body 28, typically from 5 cm to 25 cm.

The sheath body 28 may be composed of a variety of conventional non-electrically conductive catheter materials, including natural and synthetic polymers, such as polyvinyl chloride, polyurethanes, polyesters, polyethylenes, polytetrafluoroethylenes (PTFE's), nylons, PEBAX® (i.e., polyether block amide), and the like. The sheath body 28 may optionally be reinforced to enhance its strength, torqueability, and the like. Exemplary reinforcement layers include metal fiber braids, polymeric fiber braids, metal or fiber helical windings, and the like. Optionally, a portion of the sheath body 28 could be formed from a metal rod or hypotube, particularly when the sheath body 28 has a rapid exchange or monorail design.

The delivery sheath 12 further comprises a handle 36 mounted to the proximal end 30 of the sheath body 28. The handle 36 is preferably composed of a durable and rigid material, such as medical grade plastic, and is ergonomically molded to allow a physician to more easily manipulate the delivery sheath 12. The handle 36 may be mounted to the proximal end 30 of the sheath body 28 using any suitable fastening system, e.g., gluing or a compression fit.

The delivery sheath 12 further comprises an expandable member, and in particular a balloon 38, mounted to the distal end 32 of the sheath body 28. The geometry of the balloon 38 can be altered between a collapsed, low profile geometry, and an expanded, high profile geometry (shown in phantom). Preferably, the balloon 38 conforms to the maximum diameter of the sheath body 28 when in a collapsed geometry for ease of manipulation through the vasculature, and has a fully inflated diameter that is consistent with the inner diameter of the anatomical conduit intended to be occluded, typically 1-3 cm. The balloon 38 is preferably made of a suitable bio-compatible, thermoplastic or elastomeric material, such as, e.g., latex, Pebax®, C-flex®, urethane or silicone, and is preferably configured to have a cross-sectional shape consistent with the cross-sectional lumen of the anatomical conduit to be occluded. Typically, such cross-sectional shape will be circular, although other cross-sectional shapes may be used, e.g., elliptical.

As best shown in FIG. 2, the delivery sheath 12 further comprises respective inflation and venting lumens 40, 42 employed to inflate the balloon 38. In particular, the respective distal ends of the respective inflation and venting lumens 40, 42 open into a hollow interior of the balloon 38 (not shown), preferably at opposite ends thereof in order to facilitate the venting of the balloon 38. The proximal ends of the lumens 40, 42 respectively communicate with an inflation port 44 and vent port 46 located on the handle 36.

In order to inflate the balloon 38 in accordance with methods known in the art, a liquid inflation medium, such as water, saline solution, or other bio-compatible liquid is conveyed under positive pressure through the inflation port 44 and into the inflation lumen 40. Alternatively, the inflating fluid medium can comprise a gaseous medium such as carbon dioxide. The liquid medium fills the interior of the balloon 38 and exerts pressure on the inside of the balloon 38 to urge the balloon 38 from its collapsed geometry to its expanded geometry. Constant exertion of pressure through the inflation lumen 40 maintains the balloon 38 in its expanded geometry. The venting lumen 42 is used to vent any air or excess fluid from the balloon 38. Regardless of the type of inflating medium used, the inflation preferably occurs under relatively low pressures of no more than 30 psi. In particular, the pressure used depends upon the desired amount of inflation, the strength of material used for the balloon 38 and the degree of flexibility required, i.e., higher pressure results in a harder, less flexible balloon 38, when inflated.

The delivery sheath 12 further comprises a pullwire 48 that enables a user to flex the sheath body 28 into a curved geometry (shown in phantom) in order to orient the distal end 32 of the sheath body 28 in an optimal position and trajectory. The pullwire 48 extends through a pull wire lumen 34 extending through the sheath body 28, with the distal end of the pullwire 48 mounted to the distal end 32 of the sheath body 28, and the proximal end of the pullwire 48 extending out of the handle 36. Alternatively, the handle 36 can be provided with a steering mechanism, such as the one disclosed in U.S. Pat. No. 5,254,088 to Lundquist et al., which is fully and expressly incorporated herein by reference.

As best shown in FIG. 2, the delivery sheath 12 may include a support element 50 situated within the distal end 32 of the sheath body 28 to provide further rigidity, thereby allowing the sheath body 28 to be controllably flexed when the pullwire 48 is pulled, and allowing the sheath body 28 to assume a straight configuration when the pullwire 48 is relaxed. The support element 50 is preferably composed resilient, inert wire, such as nickel titanium (commercially available as Nitinol material), stainless steel 17-7, or a thermoplastic material, and is preferably rectilinear in cross-section for radially stability.

The working guidewire 14 is a heavy-duty guidewire, e.g., having a diameter of 0.038", over which the delivery sheath 12 may be introduced through the delivery lumen 34. The guidewire 14 may be composed of a suitable material, such as stainless steel. The working guidewire 14 may, e.g., have a straight tip or J-shaped tip (as illustrated in FIG. 1). The stylet 16 comprises a laterally flexible, yet axially rigid, shaft 52 and a sharpened distal tip 54 that is capable of penetrating tissue, and in particular, vascular tissue. The length of the stylet 16 is greater than the length of the sheath body 28, so that the distal end of the stylet 16 may extend from the distal end 32 of the delivery sheath 12 when fully inserted therein. The stylet 16 may be composed of a suitable material, such as stainless steel.

The ablation catheter 18 comprises an elongated catheter body 56 having a proximal end 58 and a distal end 60. The catheter body 56 may be composed of the same material as the sheath body 28 of the delivery sheath 12 and is sized to pass through the delivery lumen 34, i.e., the catheter body 56 has an outer diameter consistent with the inner diameter of the sheath body 28. The catheter body 56 has a length greater than the length of the sheath body 28, so that the distal end 60 of the catheter body 56 can extend from the distal end 32 of the sheath body 28 when fully inserted therein.

The ablation catheter 18 further comprises a plurality of electrodes 62 mounted to the distal end 32 of the catheter body 56. The electrodes 62, which are preferably composed of a conductive and biocompatible material, such as platinum-iridium or gold, are suitably mounted on the distal end 60 of the catheter body 56. In the illustrated embodiment, the electrodes 62 are rigid and are composed of solid rings pressure fitted about the catheter body 56. The electrodes 62 are separated a distance from each other, providing the catheter body 56 with nonconductive flexible regions 64 therebetween. In this manner, the distal end 32 of the catheter body 56 can be flexed in any direction, allowing the electrodes 62 to be brought into intimate contact along the tissue surface regardless of the tissue surface contour. Alternatively, the electrodes 62 can be flexible themselves, and may be composed of closely wound spiral coil electrodes or ribbon electrodes. More alternatively, the electrodes 62 can be composed of printed-on conductive ink and regenerated cellulose, which is formed by disposing bands of conductive, flexible ink over the catheter body 56, and then disposing a protective coating of regenerated cellulose over the conductive bands.

The ablation catheter 18 further comprises a handle 66 mounted to the proximal end 58 of the catheter body 56. The handle 66 is preferably composed of a durable and rigid material, such as medical grade plastic, and is ergonomically molded to allow a physician to more easily manipulate the delivery ablation catheter 18. The handle 66 may be mounted to the proximal end 58 of the catheter body 56 using any suitable fastening system, e.g., gluing or a compression fit. The handle 58 may optionally mate with the handle 36 of the delivery sheath 12 to provide an integrated handle assembly.

The ablation catheter 18 further comprises an electrical connector 68 carried by the handle 36. The electrical connector 68 is electrically coupled to electrodes 62 via one or more RF wires 70 (shown in FIG. 3) extending through the catheter body 56. The electrical connector 68 is adapted to removably mate with the RF cable 26 connected to the RF generator 22. Alternatively, the RF cable 26 may be hardwired into the electrical connector 68.

The ablation catheter 18 may optionally be equipped with a scope for providing a distal-facing view of tissue. In particular, the ablation catheter 18 comprises a distal-facing viewing window 72 mounted within distal tip of the catheter body 56, an outgoing optical fiber channel 74 and an incoming optical fiber channel 76 extending through the catheter body 56 (shown in FIG. 3), an illumination source (not shown) optically coupled to the outgoing optical fiber channel 74 via the handle 66 to illuminate the tissue around the distal tip of the ablation catheter 18, and an eye piece 78 optically coupled to the incoming optical fiber channel 76 via the handle 66 to receive images of the illuminated tissue just distal to the ablation catheter 18.

Alternatively, rather than integrating the scope with the ablation catheter 18, the scope can be a separate device 80 that can be removably introduced through a delivery lumen 82 within the ablation catheter 18, as illustrated in FIG. 4. In this case, the ablation catheter 18 may be introduced over the stylet 16, so that the ablation catheter 18 can, e.g., be conveniently guided through the puncture made within the wall of an anatomical conduit by the stylet 16.

Referring back to FIG. 1, the RF generator 22 is electrically connected to the electrical connector 68 of ablation catheter 18 via the cable 26. The RF generator 22 may be a conventional RF power supply that operates at a frequency in the range from 300 KHz to 9.5 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for tissue ablation. Thus, such power supplies would usually be operated at the lower ends of their voltage and power capabilities.

More suitable power supplies will be capable of supplying an ablation current at a relatively low voltage, typically below 150V (peak-to-peak), usually being from 50V to 100V. The power will usually be from 5 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000 (100 W) and RF3000 (200 W).

In the illustrated embodiment, RF current is delivered from the RF generator 22 to the electrodes 62 of the ablation catheter 18 in a monopolar fashion, which means that current will pass from the electrodes 62, which are configured to concentrate the energy flux in order to have an injurious effect on the distally adjacent tissue, and a dispersive electrode (not shown), which is located remotely from the electrodes 62 and has a sufficiently large area (typically 130 $cm^2$ for an adult), so that the current density is low and non-injurious to surrounding tissue. The dispersive electrode may be attached externally to the patient, e.g., using a contact pad placed on the patient's flank.

In another arrangement, the RF current is delivered to electrodes 62 in a bipolar fashion, which means that current will pass between "positive" and "negative" electrodes 62. Bipolar arrangements, which require the RF energy to traverse through a relatively small amount of tissue between the tightly spaced electrodes, are more efficient than monopolar arrangements, which require the RF energy to traverse through the thickness of the patient's body. As a result, bipolar electrodes generally create larger and/or more efficient lesions than monopolar electrodes.

The inflation medium source 20 is mated to the inflation port 44 on the handle 36 of the delivery sheath 12 via the conduit 24, so that inflation medium (e.g., saline) can be delivered from the source 20 into the interior of the balloon 38, thereby expanding the balloon 38 within an anatomical conduit in which the delivery sheath 12 resides. In the illustrated embodiment, the inflation medium source 20 comprises a standard syringe filled within the inflation medium. Alternatively, a pump or other suitable mechanism for conveying the inflation medium under positive pressure can be used.

Having described the structure of the tissue treatment system 10, its operation in treating targeted tissue within the lung of a patient via the bronchial system (i.e., the system of bronchial tubes, including the primary bronchi and any of its branches). Notably, use of the bronchial system to access lung tissue is beneficial, since convenient access to the lung tissue can be provided via a naturally occurring orifice, i.e., the patient's mouth. Also, since the bronchial system proliferates throughout the lung tissue, every region of the lung can be reached from the bronchial system. Alternatively, the arteries of the circulatory system can be used to access lung tissue. However, because the arterial system resides within the inferior regions of the lung, any tissue to be treated in the superior region of the lung cannot be reached.

While the use of the tissue treatment system 10 lends itself well to the treatment of tissue in a lung, it should be appreciated that the tissue treatment system 10 can be used to treat tissue located anywhere in the body that can be reasonably accessed from an anatomical conduit, e.g., tissue in the liver, kidney, pancreas, breast, prostrate, and the like.

Most commonly, the treatment region will comprise a solid tumor. The volume to be treated will depend on the size of the tumor or other lesion, typically having a total volume from 1 $cm^3$ to 150 $cm^3$, and often from 2 $cm^3$ to 35 $cm^3$ The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 5B:
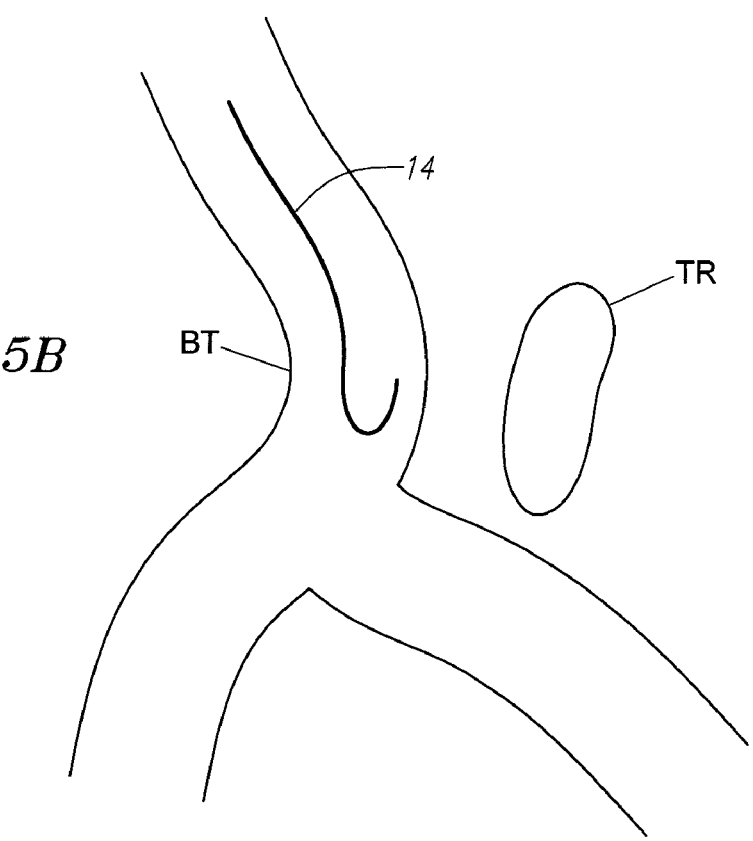
Figure 5C:
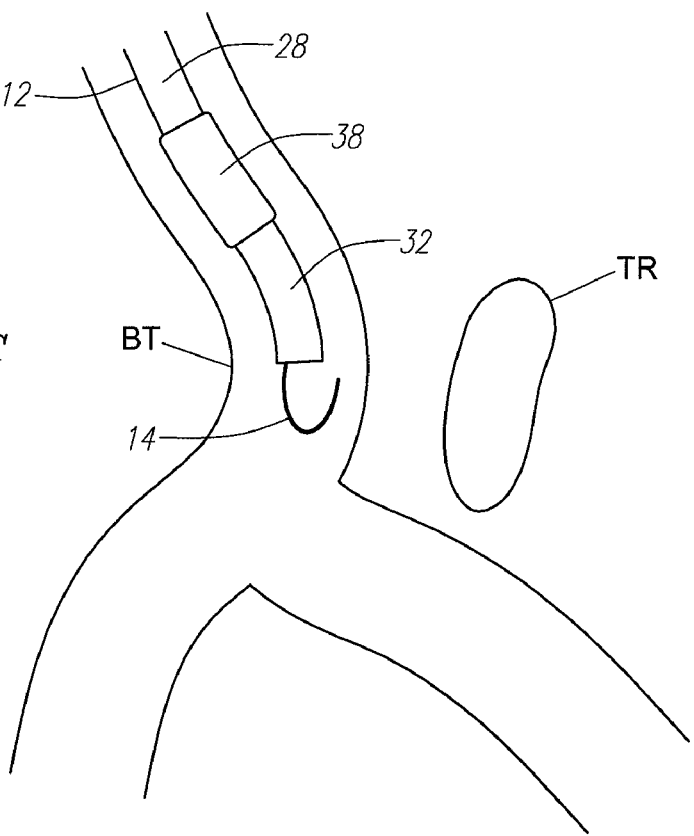

Referring to FIGS. 5A-5L, the operation of the tissue treatment system 10 is described in treating a target tissue region TR within a lung L (FIG. 5A). As can be seen, a trachea T, leads to a pair of primary bronchi PB, which further lead to secondary bronchial tubes BT. First, in a conventional manner, the guidewire 14 is introduced into the patient's mouth, in the trachea T, along the primary bronchus PB associated with the lung L that contains the target tissue region TR, and into the bronchial tube BT that supplies the target tissue region TR with air (FIG. 5B). Next, the delivery sheath 12 is introduced over the guidewire 14 until the distal end 32 of the sheath body 28 resides within the bronchial tube BT (FIG. 5C).

Figure 5D:
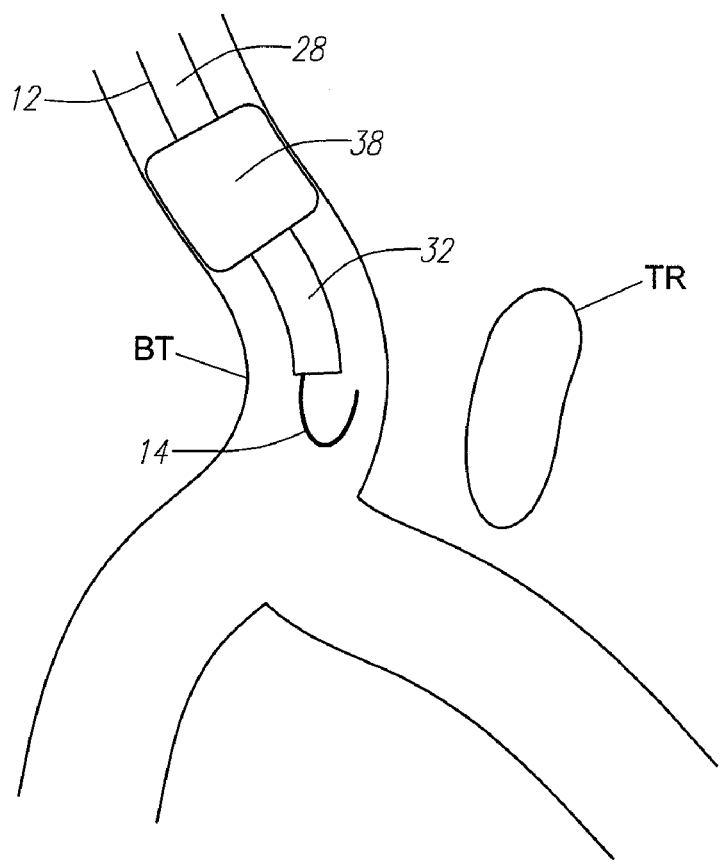

Then, the inflation medium source 20 is coupled to the inflation port 44 located on the handle 36 (located in FIG. 1) of the delivery sheath 12, and operated, so that an inflation medium is conveyed through the inflation lumen 40 (shown in FIG. 2) extending along the sheath body 28, and into the interior region of the balloon 38, thereby expanding the balloon 38 in firm contact with the wall of the bronchial tube BT (FIG. 5D). In this manner, the bronchial tube BT is at least partially occluded, and preferably totally occluded, to reduce or even prevent the flow of air through the bronchial tube BT to the tissue treatment region TR. Notably, since major blood vessels typically run parallel to air pathways in the lung, expansion of the balloon 38 within a bronchial tube BT may also constrict or partially occlude the adjacent blood vessels, thereby reducing the flow of blood through the tissue treatment region TR.

Figure 5E:
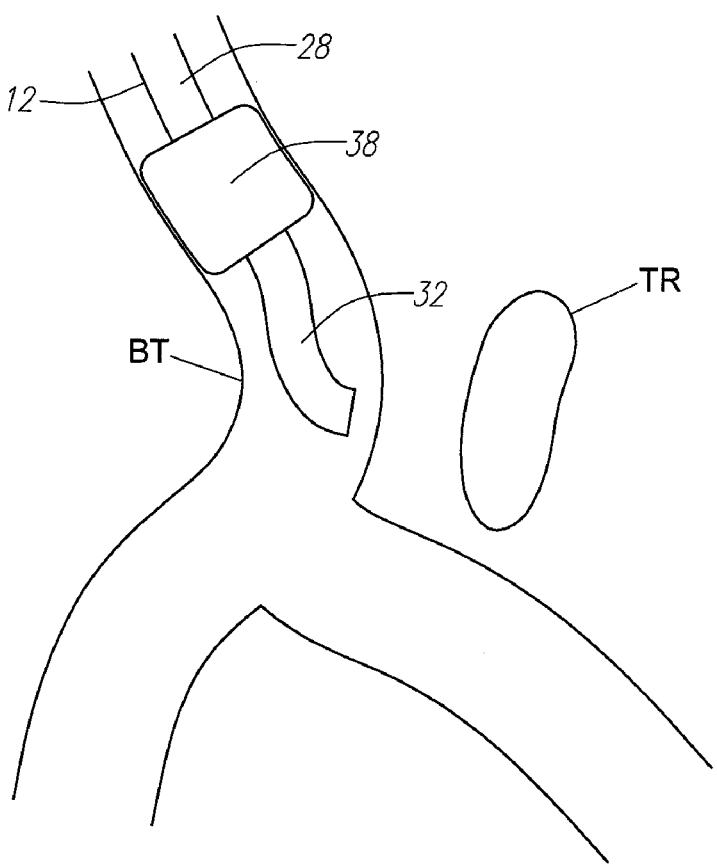
Figure 5F:
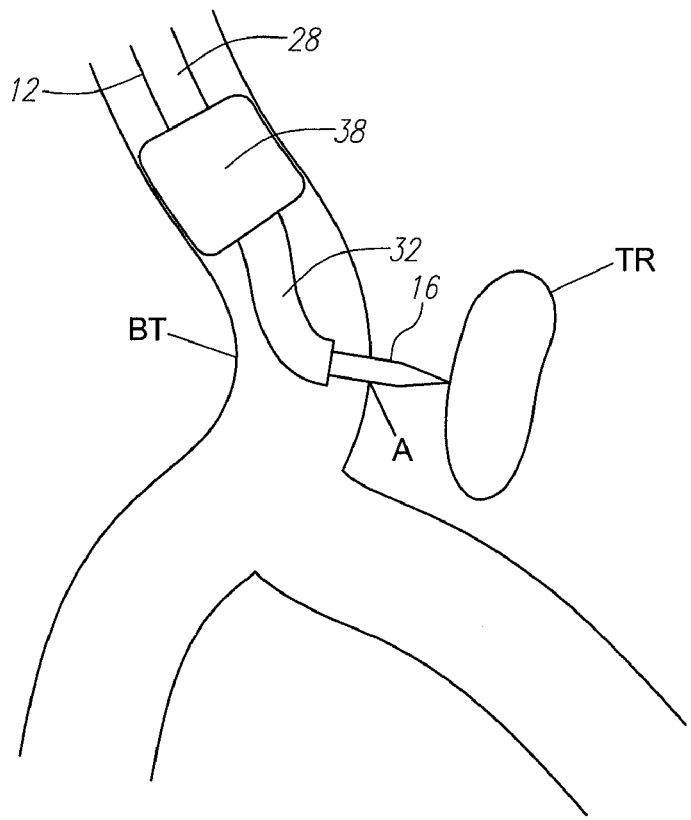

Next, the guidewire 14 is removed from the delivery sheath 12, the pullwire 48 (shown in FIG. 1) of the delivery sheath 12 is manipulated, and in particular pulled, to bend the delivery sheath 12, so that the distal end 32 of the sheath body 28 is pointing towards the region of the bronchial tube BT where a puncture is to be made (FIG. 5E). Preferably, the puncture will be in line with the trajectory along which the distal end 32 of the sheath body 28 is pointed and the tissue treatment region TR. Next, the stylet 16 is introduced through the lumen 34 of the delivery sheath 12 until the distal end 32 of the stylet 16 protrudes from the distal end 32 of the sheath body 28 and pierces the wall of the bronchial tube BT to form an aperture A (FIG. 5F). Alternatively, the stylet 16 may be introduced through the delivery sheath 12, and then the pullwire 48 manipulated to bend the distal end 32 of the sheath body 28, as well as the distal end 32 of the stylet 16, after which the stylet 16 is further advanced through the wall of the bronchial tube BT.

Figure 5G:
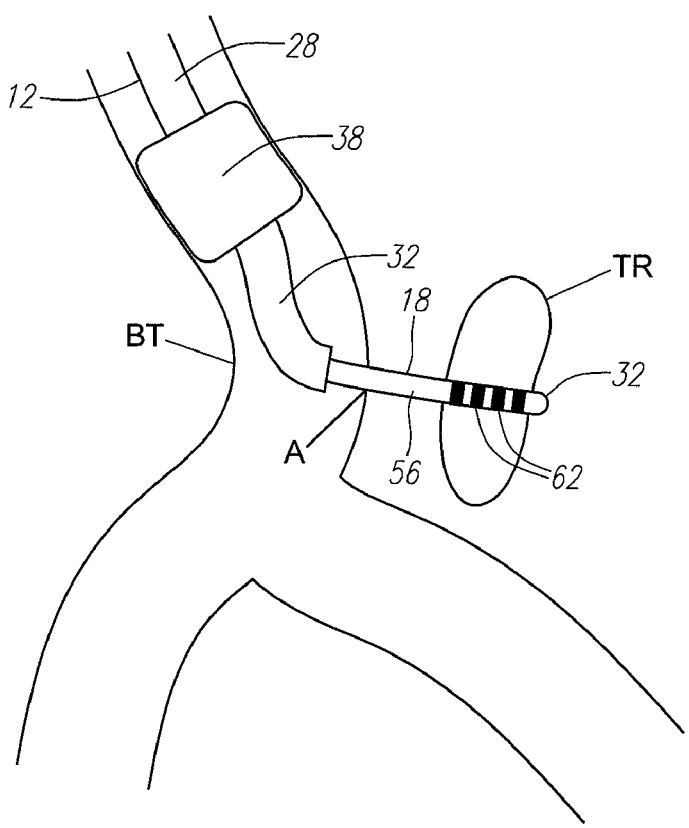

Next, the stylet 16 is removed from the delivery sheath 12, and the ablation catheter 18 is introduced through the delivery sheath 12 and advanced through the aperture A in the bronchial tube BT until the electrodes 62 reside adjacent the treatment region TR (FIG. 5G). The user may look into the eyepiece 78 (FIG. 1) of the on-board scope to visualize the tissue surrounding the distal end 32 of the ablation catheter 18 in order to navigate and ensure that the distal end 32 of the catheter body 56 is advanced through the aperture A and into the treatment region TR.

Figure 5H:
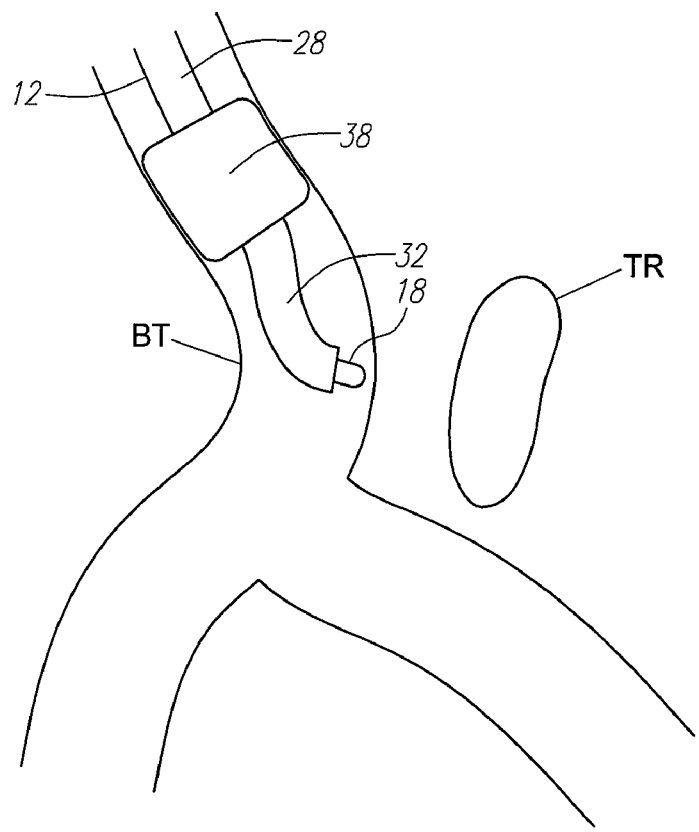
Figure 5I:
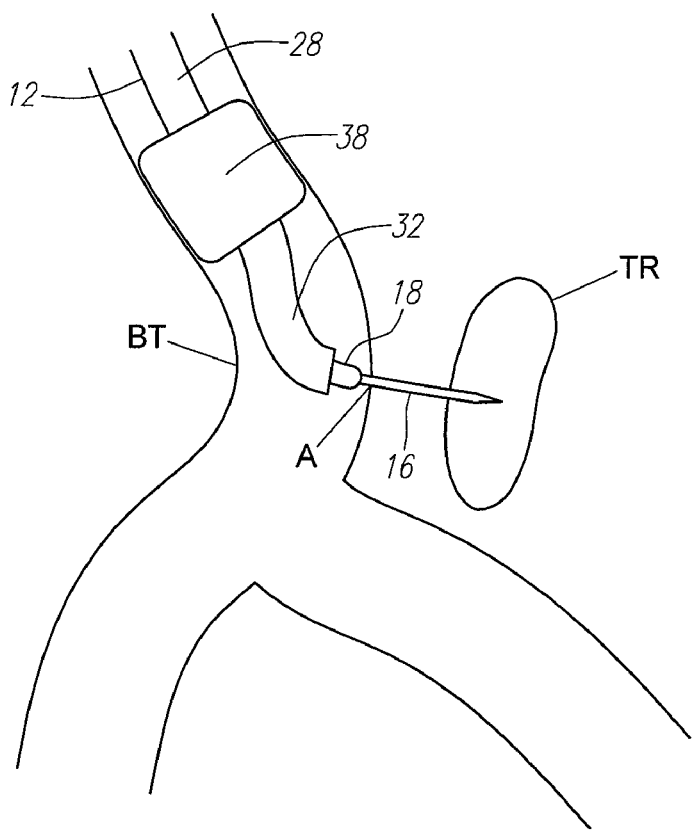
Figure 5J:
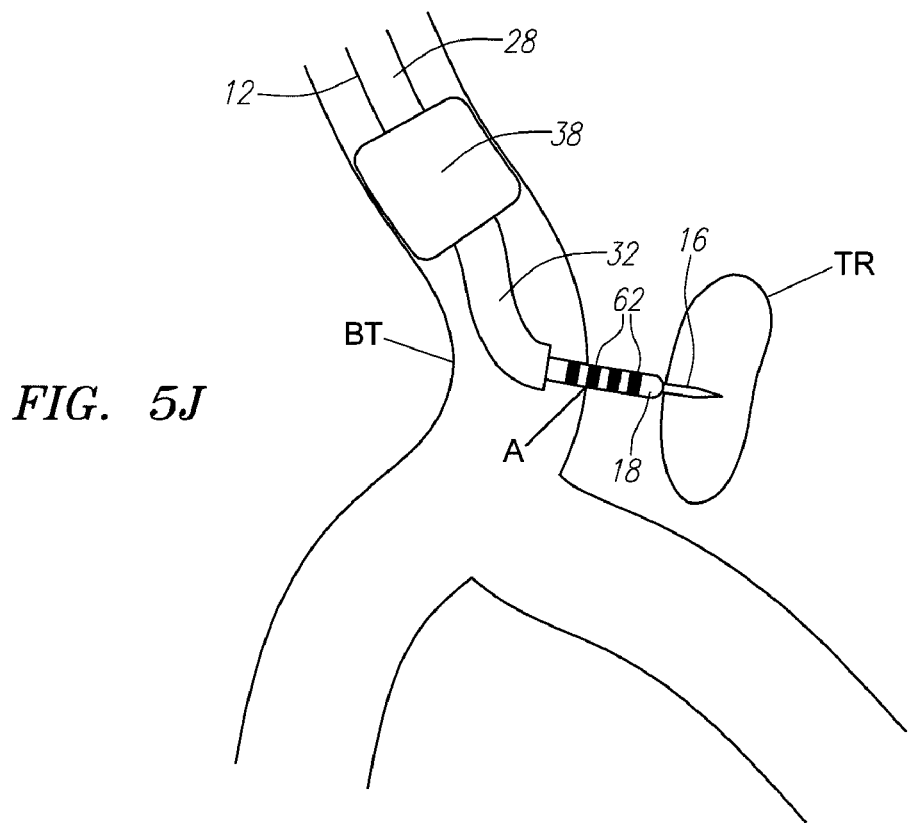

Alternatively, if a removable scope 80 (shown in FIG. 4) is used, the ablation catheter 18 can be introduced into the delivery sheath 12 prior to introducing the stylet 16, and the scope 80 introduced within the lumen 82 (shown in FIG. 4) of the ablation catheter 18 to visualize the tissue during manipulation of the pullwire 48 to ensure that the bronchial tube BT is punctured in the proper region to form the aperture A (FIG. 5H). The scope 80 can then be removed from a lumen 82 of the ablation catheter 18 and the stylet 16 introduced through the lumen 82 to pierce the bronchial tube BT (FIG. 5I). The stylet 16 can be further advanced into the treatment region TR. The ablation catheter 18 can then be advanced along the stylet 16 and through the aperture A in the bronchial tube BT until the electrodes 62 are adjacent the treatment region TR (FIG. 5J). The stylet 16 can then be removed from the lumen 82 of the ablation catheter 18, and the scope 80 reintroduced through the lumen 82 to further visualize the treatment region TR.

Figure 5K:
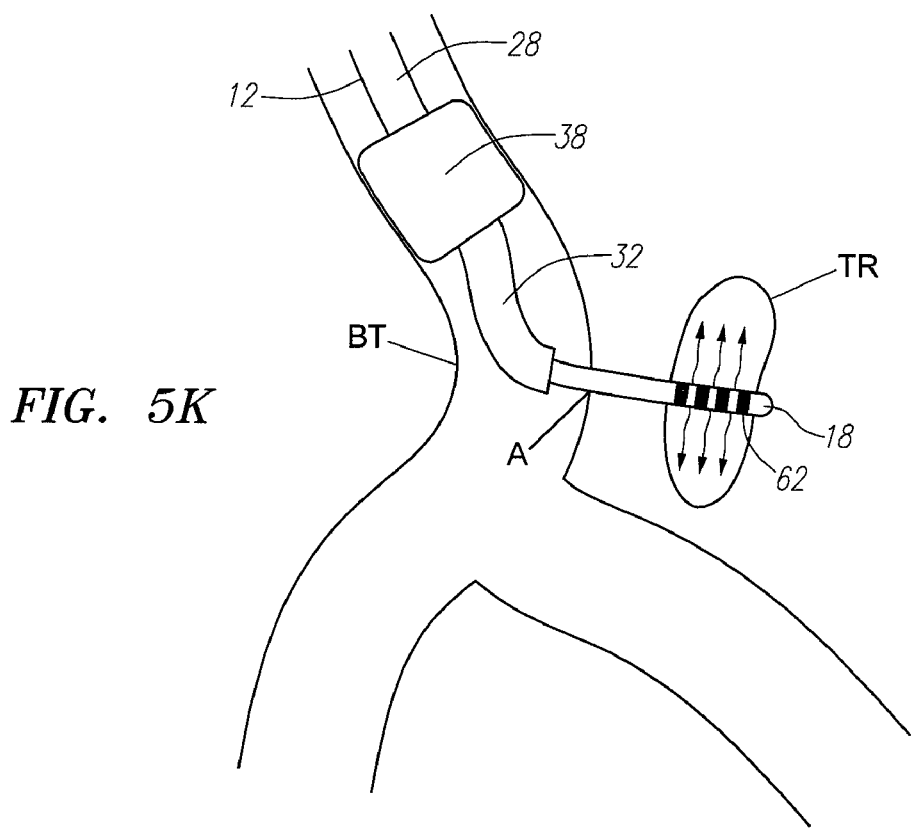
Figure 5L:
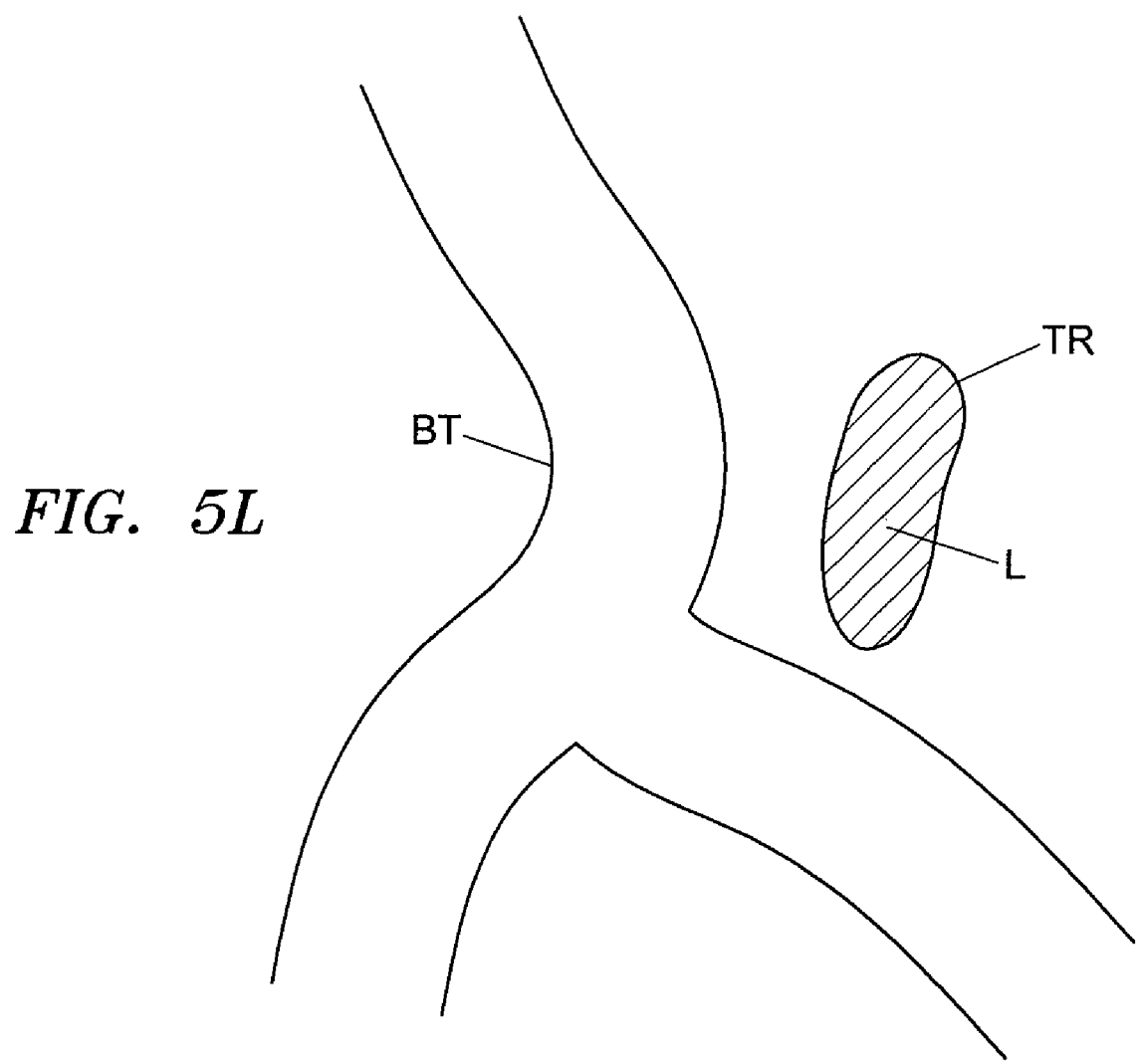

Once the ablation catheter 18 is properly positioned, the RF generator 22 (shown in FIG. 1) is coupled to the connector 68 of the ablation catheter 12 via the RF cable 26, and then operated to transmit RF energy to the electrodes 62, where the RF energy is conveyed into the tissue, thereby ablating the treatment region TR (FIG. 5K). As a result, a lesion L will be created, which will eventually expand to include the entire treatment region TR (FIG. 5L).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed:

1. A method of treating a tissue region, comprising:
    introducing a delivery sheath within an anatomical conduit, the delivery sheath comprising a pullwire extending proximally from a distal end of the delivery sheath;
    expanding an occlusive device associated with the delivery sheath, such that the conduit is at least partially occluded to reduce the flow of fluid through the conduit;
    manipulating a proximal end of the pullwire so as to bend the distal end of the delivery sheath so that the distal end is pointing towards a puncture site of the conduit adjacent the tissue region;
    introducing a tissue treatment catheter within the delivery sheath, the tissue treatment catheter having a lumen therein;
    advancing a scope within the lumen of the tissue treatment catheter to visualize the tissue region;
    removing the scope from the lumen of the tissue treatment catheter;
    introducing a stylet within the lumen of the tissue treatment catheter;
    piercing the conduit wall to create an aperture in the wall of the conduit adjacent the tissue region;
    advancing the tissue treatment catheter from the delivery sheath over the stylet and through the aperture; and
    conveying thermal energy from or to the tissue treatment catheter to treat the tissue region.

2. The method of claim 1, wherein the tissue region comprises lung tissue.

3. The method of claim 1, wherein the anatomical conduit is a blood vessel.

4. The method of claim 3, wherein the blood vessel is pulmonary artery.

5. The method of claim 1, wherein the anatomical conduit is a bronchial tube.

6. The method of claim 1, wherein the occlusive device is a balloon, and the balloon is expanded by conveying an inflation medium within an interior of the balloon.

7. The method of claim 1, wherein the occlusive device is expanded, such that the conduit is fully occluded to prevent the flow of fluid through the conduit.

8. The method of claim 1, wherein the thermal energy is conveyed from the tissue treatment catheter to treat the tissue region.

9. The method of claim 8, wherein the thermal energy is radio frequency (RF) energy.

10. The method of claim 1, wherein the thermal energy is conveyed to or from the tissue treatment catheter to ablate the tissue region.

11. The method of claim 1, further comprising:
    removing the stylet from the lumen of the tissue treatment catheter;
    reintroducing the scope within the lumen of the tissue treatment catheter; and
    visualizing the tissue region with the scope.

12. The method of claim 11, wherein visualizing comprises illuminating tissue with a first optical fiber channel operatively coupled to an illumination source and transmitting reflected light via a second optical fiber channel operatively coupled to an eye piece.

13. The method of claim 1, wherein the delivery sheath comprises a support element disposed in the distal end of a sheath body configured to impart a straight configuration to a sheath body when the pullwire is relaxed.

14. The method of claim 1, wherein the distal end of the delivery sheath is bent without the presence of the stylet.

15. The method of claim 1, wherein the distal end of the delivery sheath is bent with the presence of the stylet.

16. The method of claim 1, further comprising introducing a guidewire within the anatomical conduit and advancing the delivery sheath over the guidewire.

* * * * *